(12) United States Patent
Khosrowshahi (10) Patent No.: US 8,585,665 B2
(45) Date of Patent: Nov. 19, 2013

(54) TRANSMISSIVE DRESSING FOR NEGATIVE PRESSURE WOUND THERAPY

(75) Inventor: Hamid Khosrowshahi, Tarrytown, NY (US)

(73) Assignee: Prospera Technologies LLC, Fort Worth, TX (US)

( * ) Notice: Subject to any disclaimer, the term of this patent is extended or adjusted under 35 U.S.C. 154(b) by 144 days.

(21) Appl. No.: 13/175,272

(22) Filed: Jul. 1, 2011

(65) Prior Publication Data

US 2012/0029449 A1    Feb. 2, 2012

Related U.S. Application Data

(60) Provisional application No. 61/360,834, filed on Jul. 1, 2010.

(51) Int. Cl.
*A61M 1/00* (2006.01)
*A61M 27/00* (2006.01)

(52) U.S. Cl.
USPC .......................................... 604/315; 604/543

(58) Field of Classification Search
USPC ........................ 604/180, 313–316, 540–543
See application file for complete search history.

(56) References Cited

U.S. PATENT DOCUMENTS

| | | | |
|---|---|---|---|
| 5,074,847 A * | 12/1991 | Greenwell et al. | 604/174 |
| 2007/0027414 A1 * | 2/2007 | Hoffman et al. | 602/2 |
| 2010/0305524 A1 * | 12/2010 | Vess et al. | 604/313 |

FOREIGN PATENT DOCUMENTS

| | | |
|---|---|---|
| DE | 202009013208 | 3/2010 |
| DE | 202009016141 | 4/2010 |

* cited by examiner

*Primary Examiner* — Jackie Ho
*Assistant Examiner* — Mark K Han
(74) *Attorney, Agent, or Firm* — Bracewell & Giuliani LLP (57) ABSTRACT

An apparatus and method for treating a wound can include a flexible sheet for sealingly engaging a patient's skin around a wound bed, a drain to be located in the wound bed, a vacuum source connected to the drain, and a flow restriction device to control the flow of fluid through an aperture of the flexible sheet.

11 Claims, 5 Drawing Sheets

TRANSMISSIVE DRESSING FOR NEGATIVE PRESSURE WOUND THERAPY

CROSS-REFERENCE TO RELATED APPLICATIONS

This application claims the benefit of the filing date of U.S. Provisional Patent Application No. 61/360,834, filed on Jul. 1, 2010.

BACKGROUND OF THE INVENTION

1. Field of the Invention

This invention generally relates to the field of negative pressure wound therapy dressings. In particular, the present invention is directed to a method and apparatus for establishing a pressure differential between a wound bed and a suction apparatus during the application of negative pressure wound therapy.

2. Brief Description of Related Art

Negative pressure can be used to treat various types of wounds. In some applications, the negative pressure can be applied to the wound via a vacuum source and a dressing. The negative pressure can be used to drain fluid and exudates from the wound, and can also stimulate blood flow in the tissue of the wound bed, thus promoting healing.

Improper flow from the wound bed toward the vacuum source can make the negative pressure less effective. For example, if the flow rate is too high, a vacuum source, such as a pump, must run more often, which can lead to premature pump failure. If the flow is too low, then fluids located in the wound bed can stagnate in the wound bed rather than being drained. Therefore, it is desirable to control the flow of fluid from the wound bed.

SUMMARY OF THE INVENTION

In one embodiment of an apparatus for treating wounds using negative pressure can include a drain, a flexible sheet for covering a wound bed, the flexible sheet having a dressing aperture. The flexible sheet can sealingly engage tissue proximate to the wound bed while the drain is located between the flexible sheet and the wound bed. The dressing can also include a tube in communication with the drain and a flow restriction device covering the dressing aperture. The flow restriction device can reduce the flow of vapor and substantially prevent the flow of liquid through the aperture.

In one embodiment, the transmissive patch can have a higher rate of vapor transmission than the flexible sheet. The flexible sheet can be semi-permeable to vapor and generally impermeable to liquid. A vacuum source can be connected to and in communication with the tube. The vacuum source can create a negative pressure at the vacuum source, the negative pressure can be communicated through the tube and drain to the wound bed, and the pressure in the wound bed can thus be greater than the pressure at the vacuum source.

In one embodiment, the flow restriction device can include high-density polyethylene fibers. Indeed, the flow restriction device can have a predetermined vapor transmission rate at a given pressure. The flow restriction device can include a semi-permeable barrier and an adhesive, the adhesive forming a seal between the flow restriction device and the flexible sheet. The flow restriction device can include a semi-permeable barrier located between a first layer having a first aperture and a second layer having a second aperture, and at least a portion of the second layer can sealingly engage the flexible sheet and the second aperture can be in communication with the aperture.

In one embodiment, a method for treating a wound is described. The method can include the steps of placing a drain tube in a wound bed; covering the drain tube and wound bed with a flexible sheet, the space between the flexible sheet and the wound bed defining a dressing space; creating a dressing aperture in the flexible sheet; covering the dressing aperture with a flow restriction device; connecting a vacuum source to the drain tube; creating negative pressure at the vacuum source; and creating a pressure differential between the negative pressure at the vacuum source and the wound bed to allow a vapor to flow from the dressing space to the vacuum source.

In one embodiment of the method, the vacuum source can include a pump, and the method can include the step cycling the pump on and off and maintaining the negative pressure at the vacuum source for at least a predetermined amount of time while the pump is off. The pressure differential can be sufficient to move fluids from the dressing space toward the vacuum pump. The flow restriction device can include a semi-permeable layer located between a first layer having a first aperture and a second layer having a second aperture, wherein at least a portion of the second layer sealingly engages the flexible sheet and the second aperture is in communication with the dressing aperture, and including the step of flowing a vapor through the first aperture, through the semi-permeable layer, through the second aperture, and through the dressing aperture. A flow rate through the flow restriction device, at a given level of negative pressure, can be determined by a lateral distance between the first aperture and the second aperture. The pump can include a low-flow alarm, and the flow through the flow restriction device can be sufficiently high to prevent actuation of the low-flow alarm during normal operation. One step can include perforating the flexible sheet to create the dressing aperture after the flexible sheet is covering the wound bed and another step can include adhering a vent patch having a semi-permeable membrane and an adhesive, to the flexible sheet such that the semi-permeable membrane covers the dressing aperture. In one embodiment, the vapor flow rate through the flow restriction device is greater than the flow rate through the flexible sheet.

In one embodiment, a system for treating a wound is described. The system can include a flexible sheet that can cover a wound bed and sealingly engage the skin adjacent to the wound bed. The space between the flexible sheet and the wound bed is defined as a dressing space. The system can also include an aperture through the flexible sheet, a flow restriction device covering the aperture and sealingly engaging the flexible sheet, the flow restriction device permitting vapor to pass through it while preventing liquid from passing through it, a drain located within dressing space, packing located within dressing space, a tube in communication with the drain, and a vacuum source in communication with the drain. In one embodiment, the flow restriction device can include a membrane and an adhesive, the adhesive preventing liquid from traveling past a perimeter of the membrane. In one embodiment, the flow rate of vapor passing through the flow restriction device can be greater than a flow rate of vapor passing through the flexible sheet.

BRIEF DESCRIPTION OF THE DRAWINGS

So that the manner in which the features, advantages and objects of the invention, as well as others which will become apparent, are attained and can be understood in more detail, more particular description of the invention briefly summarized above may be had by reference to the embodiment thereof which is illustrated in the appended drawings, which drawings form a part of this specification. It is to be noted, however, that the drawings illustrate only a preferred embodiment of the invention and is therefore not to be considered limiting of its scope as the invention may admit to other equally effective embodiments.

DETAILED DESCRIPTION OF THE PREFERRED EMBODIMENT

The present invention will now be described more fully hereinafter with reference to the accompanying drawings which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout, and the prime notation, if used, indicates similar elements in alternative embodiments.

Figure 1:
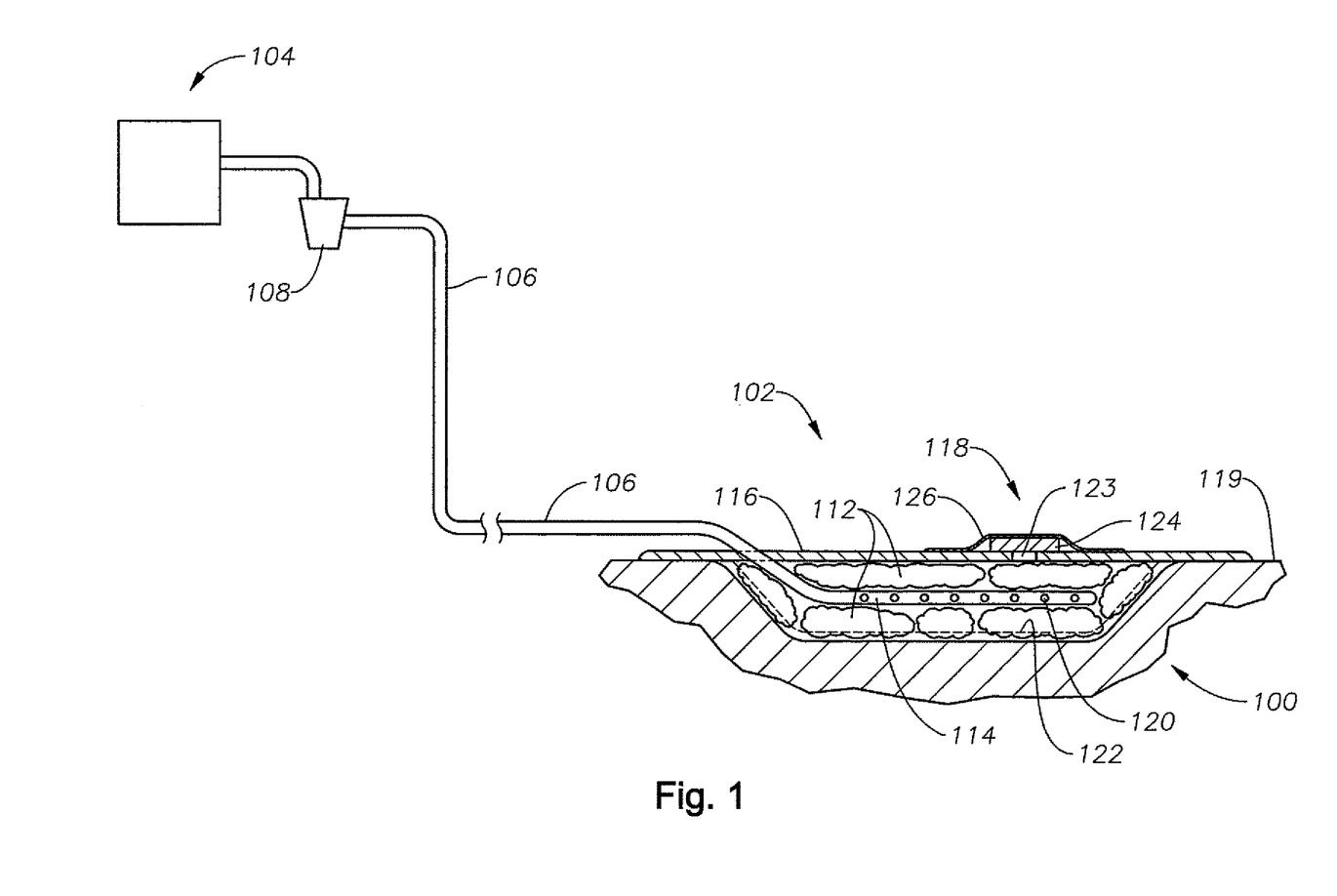
FIG. 1 is a sectional side-view of an exemplary embodiment of a negative pressure wound therapy apparatus having a transmissive patch.
Figure 2:
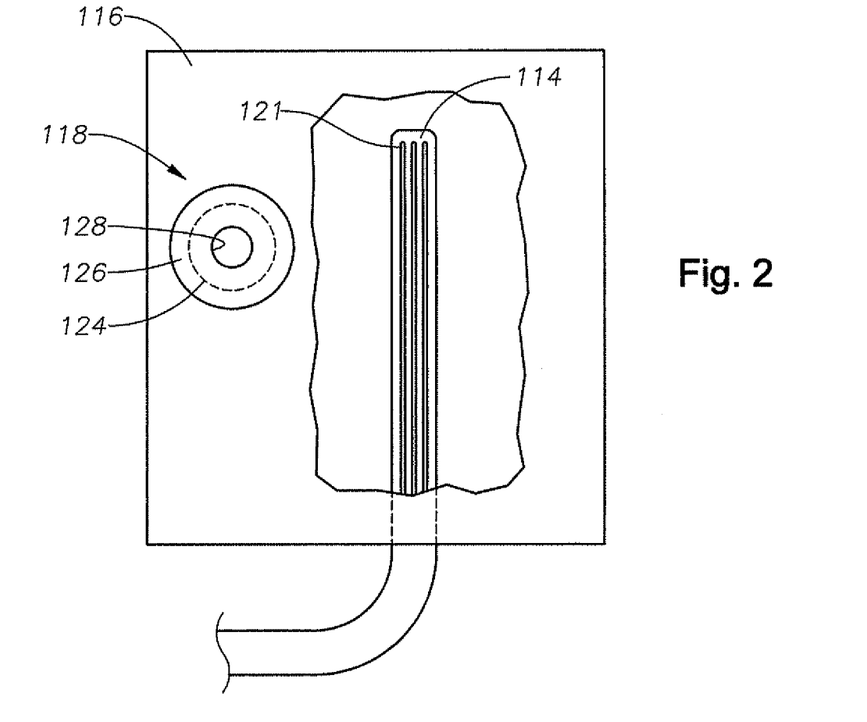
FIG. 2 is a partial cut-away top view of the negative pressure wound therapy apparatus of claim 1.

Referring to FIGS. 1 and 2, negative pressure wound therapy involves the application of negative pressure to a wound to facilitate wound closure. The wound 100 can be any open wound such as an acute or chronic wound on the surface of the skin, a fistulae, an incision, and the like. The negative pressure at the wound 100 can remove exudates and bacteria and can also promote the flow of blood in capillaries near the wound. Negative pressure wound therapy ("NPWT") treatment can include a negative pressure wound therapy dressing ("dressing") 102 over a wound 100 and a vacuum source 104 for maintaining negative pressure. In one embodiment, vacuum source 104 is connected to dressing 102, via vacuum tube 106, to create the negative pressure. The vacuum source 104 can be, for example, any type of vacuum pump or facility vacuum line, including, for example, an electric pump, a battery powered pump, a mechanical suction device, a wall suction line in a hospital, and the like. Vacuum source 104 may operate continuously, cycle between high and low levels of negative pressure (variable), or cycle on and off (intermittent) while applying negative pressure. Negative pressure could be any level of negative pressure, including, for example, between about 0.1 mmHg and 200 mmHg. In one embodiment, the negative pressure is maintained at a set point between about 20 mmHg and 125 mmHg. In one embodiment, the negative pressure is maintained at a point between about 40 mmHg and 80 mmHg. In an embodiment having variable negative pressure, the negative pressure can oscillate between, for example, 40 mmHg and 80 mmHg. In some embodiments, vacuum source 104 is able to detect flow, or the lack thereof, of air and other fluids moving through vacuum source 104. A lack of flow, or "no-flow" condition, can be caused by a variety of conditions, including, for example, a kinked or blocked vacuum tube 106, exudates in drain 114, a full collection canister 108, an occluded filter (not shown), or stagnant flow wherein there is insufficient pressure differential to draw the exudates through the tube 106 to collection canister 108. In some embodiments, vacuum source 104 can stop the application of negative pressure, such as by stopping the pump motor, if flow is inadequate.

Collection canister 108 can be located between the vacuum source 104 and dressing 102 for collecting fluids drawn from the wound bed 100. In some embodiments, collection canister 108 has one or more devices (not shown) for preventing fluids from overflowing the canister and contaminating vacuum source. For example, a sensor on canister 108 or proximate to the canister may stop vacuum source 104 when fluid reaches a predetermined level in collection canister. Alternatively, a hydrophobic filter may be located in collection canister or in tubing between collection canister and vacuum source such that all air drawn by vacuum source is pulled through hydrophobic filter. If fluid contacts the hydrophobic filter, the filter becomes occluded and blocks flow from the canister. A sensor on vacuum source 104 may stop vacuum source 104, such as by turning off a pump, when the filter becomes occluded. Some embodiments may have a float valve that closes when fluid reaches a predetermined level in canister 108 and thus prevent fluids from overflowing canister.

Dressing 102 is placed over wound bed 100. Dressing 102 can include a wound contact layer, or interface layer, such as, for example, packing 112 (packing is also known as wound filler), drain 114 connected to tube 106, thin flexible sheet 116 to provide a seal, and a flow restriction device such as transmissive patch 118. In an exemplary embodiment, the packing 112 used to pack the wound can be, for example, fluffed gauze, foam, natural or synthetic polymers, and the like. Packing 112 may promote a more even distribution of negative pressure across wound bed 100. Other materials, such as hydrophobic polymers (not shown), hydrophobic synthetic polymers (not shown), or anti-bacterial dressings, such as, for example, silver impregnated dressings, may be placed above or below packing 112 to reduce bacterial growth within the wound or to promote a more even pressure distribution in the vicinity of the wound.

Drain 114 may be placed in or above wound bed 100. In an exemplary embodiment, drain 114 is placed over a layer of packing 112. Drain 114 may be tubing having a plurality of apertures 120. Alternatively, drain 114 may be tubing having one or more channels 121 (FIG. 2) in an outer diameter surface running in an axial direction along all or a portion of the length of drain 114. Drain 114 may be in communication with vacuum tube 106 and thus be in communication with collection canister 108 and vacuum source 104. In some embodiments, additional packing 112 may be placed above drain 114.

Referring to FIG. 2, flexible sheet 116 is placed over wound bed 100 to form a seal. In a preferred embodiment, flexible sheet 116 is transparent, thus allowing caregiver to see the condition of dressing and wound bed. Flexible sheet 116 may be sealed to tissue, such as skin 119, surrounding or proximate to the wound bed 100. In some embodiments, flexible sheet 116 has an adhesive coating (not shown) on one side, or around the perimeter of one side, for forming a seal against skin 119. Other techniques for forming a seal between flexible sheet 116 and skin 119 can be used.

Flexible sheet 116 can be a semi-permeable material. A semi-permeable material allows some gas to pass through the material but substantially prevents liquids from passing through. In some embodiments, semi-permeable sheets allow vapor to pass through at a moisture vapor transmission rate ("MVTR") of roughly 22-55, as determined by MVTR Method ASTM E96 Method E. Examples of suitable flexible sheets 116 include Bioclusive™, Tegaderm™, Opsite®, and Transeal™. Other types of flexible sheets 116 may be used and higher or lower MVTRs may be used. Alternatively, an impermeable or generally impermeable flexible sheet 116 can be used.

Referring again to FIG. 1, when negative pressure is created by vacuum source 104 via tubing 106, the negative pressure is communicated to the space between flexible sheet 116 and wound bed 100. This space is identified as dressing space 122. Dressing space 122 is all or partially occupied by packing 112, drain 114, and at times, wound exudate. It is desirable for a pressure differential to exist between dressing space 122 and vacuum source 104, wherein any fluids present in dressing space 122 are drawn, as a result of negative pressure at vacuum source 104, toward collection canister 108. If air or liquid fluids are not introduced into dressing space 122, then exudates and other fluids may not move away from dressing space 122 toward the vacuum source 104, thus resulting in pooling, or a buildup of fluids, within dressing space 122.

If the surface area of the flexible sheet 116 is sufficiently large, a small amount of air, or other gas, may be able to pass through flexible sheet 116 into dressing space 122. Air flow into dressing space 122 causes a slight pressure differential. The pressure differential promotes the movement of air and fluids from dressing space 122 toward vacuum source, wherein fluids can be collected by collection canister 108. In some situations, the flow through semi-permeable flexible sheet 116 is less than desired. This can occur when, for example, the surface area of flexible sheet 116 is too small and the wound drainage is not sufficient to introduce a significant amount of fluid into the wound bed. It can also occur if the MVTR of the flexible sheet 116 is less than desired. Inadequate flow may result in stagnation of fluids and exudates in dressing space 122, tubing 106, or in drain 114. Furthermore, lack of flow may cause vacuum source 104 to generate an alarm, such as an occluded line, full-canister, or any other type of low/no-flow alarm.

Dressing aperture 123 may be used to admit air or other gases into dressing space 122. Dressing aperture 123 can be a hole or opening through flexible sheet 116. Dressing aperture may be a simple pin-hole, a slit, or may be a larger opening in flexible sheet 116. In one embodiment, dressing aperture 123 can be approximately 1-3 mm in diameter. Preferably, dressing aperture 123 in flexible sheet 116 is smaller than transmissive patch 118. An opening in flexible sheet 116 that is not covered by a flow restriction device may admit too much air into dressing space 122. A flow restriction device, such as, for example, transmissive patch 118, may be used to reduce the flow of vapor and substantially prevent the flow of liquid through dressing aperture 123. Indeed, the flow restriction device can restrict the types and volumes of material passing through dressing aperture 123 while still passing gas or vapor at a higher rate than would otherwise pass through flexible sheet 116.

Figure 3:
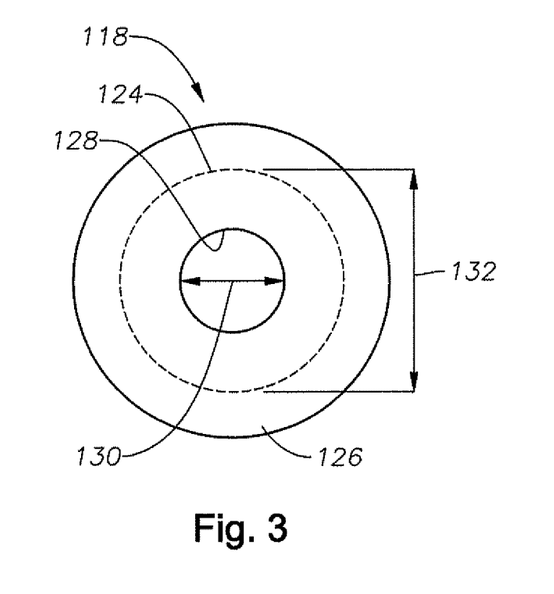
FIG. 3 is a detailed top-view of an embodiment of the transmissive patch of the negative pressure wound therapy apparatus of FIG. 1.

Referring to FIG. 2, transmissive patch 118 can have a semi-permeable barrier 124 and can have cover layer 126. Cover layer 126 may be used to hold and seal semi-permeable barrier 124 in place. Semi-permeable barrier 124 can be considered semi-permeable, in that in some embodiments, it can pass gas and other vapor at a restrictive rate, but does not allow liquids, bacteria, or germs to pass through. In one embodiment, liquids, bacteria, or germs are not able to pass through semi-permeable barrier 124 in either direction. In an exemplary embodiment, semi-permeable barrier 124 may be made out of a "breathable" material such as flashspun high-density polyethylene fibers. A commercial embodiment of a suitable material is sold under the brand name Tyvek®. Other materials that block liquid and germ transmission but allow gas and vapor transmission may be used for semi-permeable barrier 124. Preferably, the transmission rates of semi-permeable barrier 124 are higher than the transmission rates of flexible sheet 116. Semi-permeable barrier 124 may be any shape including, for example, round, square, or rectangular. Semi-permeable barrier 124 may be any size. In an exemplary embodiment, semi-permeable barrier 124 is roughly 2-3 mm in diameter, but may be larger or smaller to allow more or less flow through semi-permeable barrier 124. Preferably, the size of semi-permeable barrier 124 is smaller than the size of flexible sheet 116. Semi-permeable barrier 124 can be any thickness. In one embodiment, the thickness of semi-permeable barrier 124 is selected to facilitate a particular rate of vapor transmission. In this embodiment, a thicker layer of semi-permeable barrier 124 can be selected to cause a lower rate of vapor transmission.

The rate at which air passes through semi-permeable barrier 124 is determined by the type and density of the semi-permeable barrier material, the thickness of the semi-permeable barrier material, and the surface area of the semi-permeable barrier material. In an exemplary embodiment, the semi-permeable barrier 124 is selected to permit a predetermined amount of air to pass through at a given level of negative pressure. Preferably, semi-permeable barrier 124 passes enough air to create an appropriate pressure differential between dressing space 122 and vacuum source 104. An appropriate pressure differential is one that is sufficient to cause fluids to move from the dressing space 122 toward vacuum source 104. Preferably, semi-permeable barrier 124 also provides sufficient flow restriction to maintain negative pressure within dressing space 122. Such sufficient flow conditions can reduce the occurrence of a low-flow or "check dressing seal" alarm.

In some embodiments, vacuum source 104 is a pump unit wherein the pump motor cycles on when the negative pressure level drops below a certain level. If flow through dressing aperture 123 is too high, the pump motor would have to run constantly or at least frequently, which could lead to premature pump failure. In a preferred embodiment, flow through semi-permeable barrier 124 is low enough to maintain negative pressure in dressing space 122 for a period of time while pump motor is cycled off. In other words, pump motor does not have to run constantly to maintain a level of negative pressure. Furthermore, if too much air flows through dressing space 122, the wound bed or dressing components, such as packing 112, may become too dry. The flow through semi-permeable barrier 124 is low enough to prevent the wound bed and dressing components from drying out.

Cover layer 126 can be used to secure semi-permeable barrier 124 to flexible sheet 116. In an exemplary embodiment, cover layer 126 is an adhesive, flexible cover made of a semi-permeable material such as Bioclusive™, Tegaderm™, Opsite®, or Transeal™. Cover layer 126 can be a permeable, semi-permeable, or impermeable material.

In an exemplary embodiment, cover layer 126 is larger than semi-permeable barrier 124 and thus a perimeter of cover layer 126 extends beyond semi-permeable barrier 124. The adhesive coating of cover layer 126 can sealingly engage cover layer 126 to flexible sheet 116, thus preventing fluids from leaking past transmissive patch 118. Cover layer 126 can have one or more openings 128 to permit ambient air to directly contact the surface of semi-permeable barrier 124. Because air is able to pass through openings 128 of cover layer 126, the permeability of cover layer 126 does not significantly impact the overall permeability of transmissive patch 118. As shown in FIG. 3, cover layer 126 may be an annular ring with a central opening 128, the central opening 128 having diameter 130 that is smaller than diameter 132 of semi-permeable barrier 124. In this embodiment, semi-permeable barrier 124 is a round disc, with a diameter 132 that is larger than central opening 128 but smaller than the outer diameter of cover layer 126.

Figure 4:
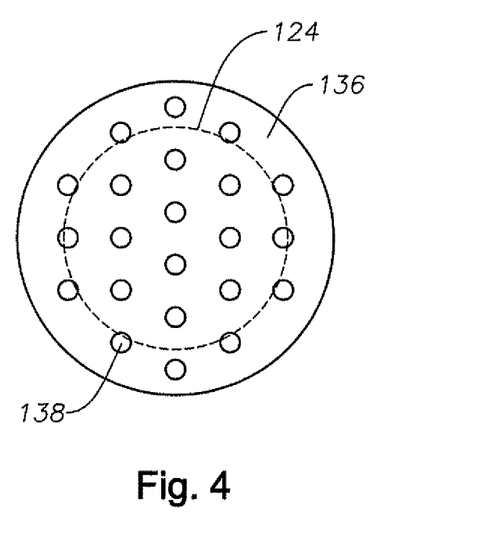
FIG. 4 is a top-view of an alternative embodiment of the transmissive patch of the negative pressure wound therapy apparatus of FIG. 1.

Referring to FIG. 4, in an alternative embodiment, cover layer 136 is a disc having a diameter greater than the diameter of disc-shaped semi-permeable barrier 124. Cover layer 136 is perforated with multiple apertures 138 for passing air through cover layer 136 to the surface of semi-permeable barrier 124. Apertures 138 may be round, square, or any other shape.

Figure 5:
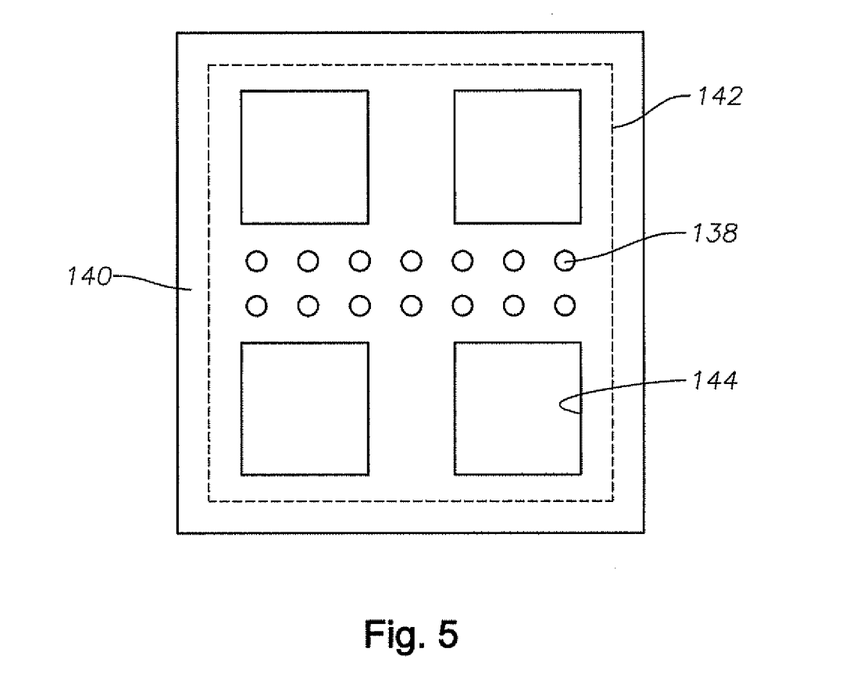
FIG. 5 is a top-view of another alternative embodiment of the transmissive patch of the negative pressure wound therapy apparatus of FIG. 1.

Referring to FIG. 5, in another alternative embodiment, cover layer 140 and semi-permeable barrier 142 each have a rectangular shape. The edges of cover layer 140 extend beyond the edges of semi-permeable barrier 142. Cutouts 144 on cover layer 140 expose the surface of semi-permeable barrier 142. Cutouts 144 may be round, square, rectangular, or any other shape.

Figure 6:
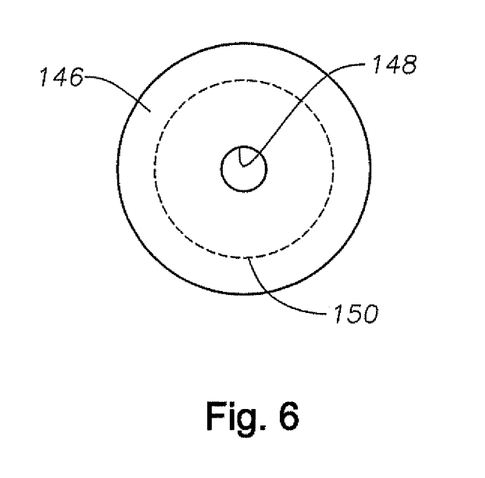
FIG. 6 is a top-view of another alternative embodiment of the transmissive patch of the negative pressure wound therapy apparatus of FIG. 1.

Referring to the alternative embodiment of FIG. 6, cover layer 146 has a single opening 148. Semi-permeable barrier 150 is a round disc having a 2-3 mm diameter and is centered on the single opening 148 of cover layer 146.

Figure 7:
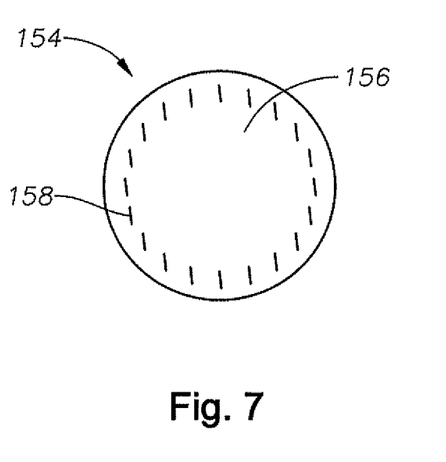
FIG. 7 is a top-view of another alternative embodiment of the transmissive patch of the negative pressure wound therapy apparatus of FIG. 1.

Referring to FIG. 7, in another alternative embodiment, vent patch 154 can be a semi-permeable barrier 156 without a cover layer. Adhesive 158 can be located around the outer edge and used to adhere vent patch 154 to flexible sheet 116 (FIG. 1).

Figure 8:
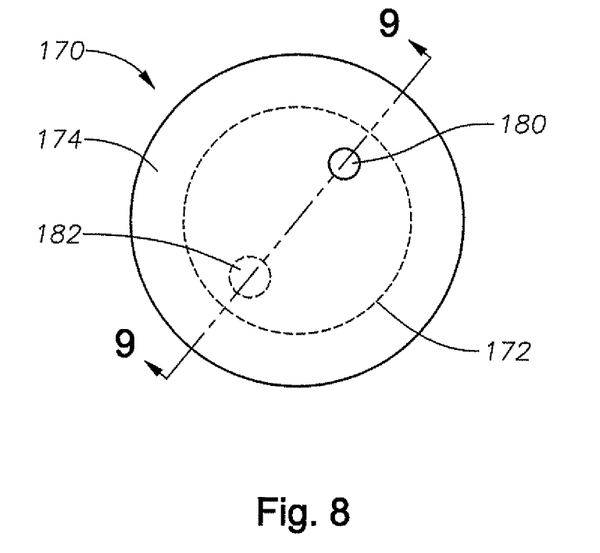
FIG. 8 is a top-view of another alternative embodiment of the transmissive patch of the negative pressure wound therapy apparatus of FIG. 1.
Figure 9:
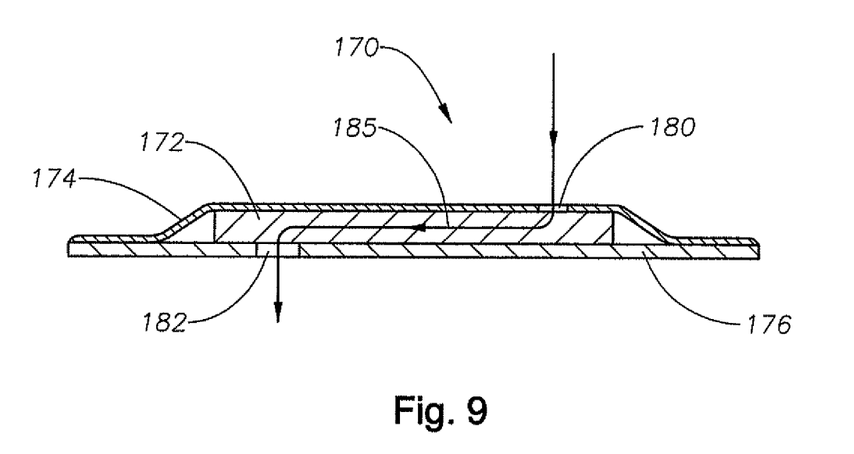
FIG. 9 is a sectional view of the embodiment of the transmissive patch of FIG. 8, taken along the 9-9 line.

Referring to FIGS. 8 and 9, vent patch 170 can include a semi-permeable barrier 172 that is sandwiched between cover layer 174 and adhesive layer 176. One side of cover layer 174 can have an adhesive for adhering to semi-permeable barrier 172 and adhesive layer 176. Similarly, adhesive layer 176 can have an adhesive coating on one side for adhering to flexible sheet 116 (FIG. 1). Either or both of cover layer 174 and adhesive layer 176 can have adhesive coatings. Vent patch 170 can be any shape including, for example, round, rectangular, or elliptical.

Inlet aperture 180 can be a hole or other perforation through cover layer 174. Outlet aperture 182 can be a hole or other perforation through adhesive layer 176. In one embodiment, the adhesive of adhesive layer 176 is used to adhere vent patch 170 onto flexible sheet 116. In a preferred embodiment, outlet aperture 182 is located over dressing aperture 123. Inlet and outlet apertures 180, 182 can each be any size. They can be, for example, 1 mm in diameter, a pin-hole, or any other size or shape. In one embodiment, outlet aperture 182 is larger than inlet aperture 182 which can make it easier to align outlet aperture 182 with dressing aperture 123.

When suction is applied to dressing space 122 (FIG. 1), flow path 185 is created, wherein air or other fluid located outside of vent patch 170 passes through inlet aperture 180, through semi-permeable barrier 172, through outlet aperture 182, through dressing aperture 123 (FIG. 1), and into dressing space 122 (FIG. 1). The rate of fluid flow is controlled by the thickness of semi-permeable barrier 170, the lateral distance between inlet aperture 180 and outlet aperture 182, and the level of negative suction.

Figure 10:
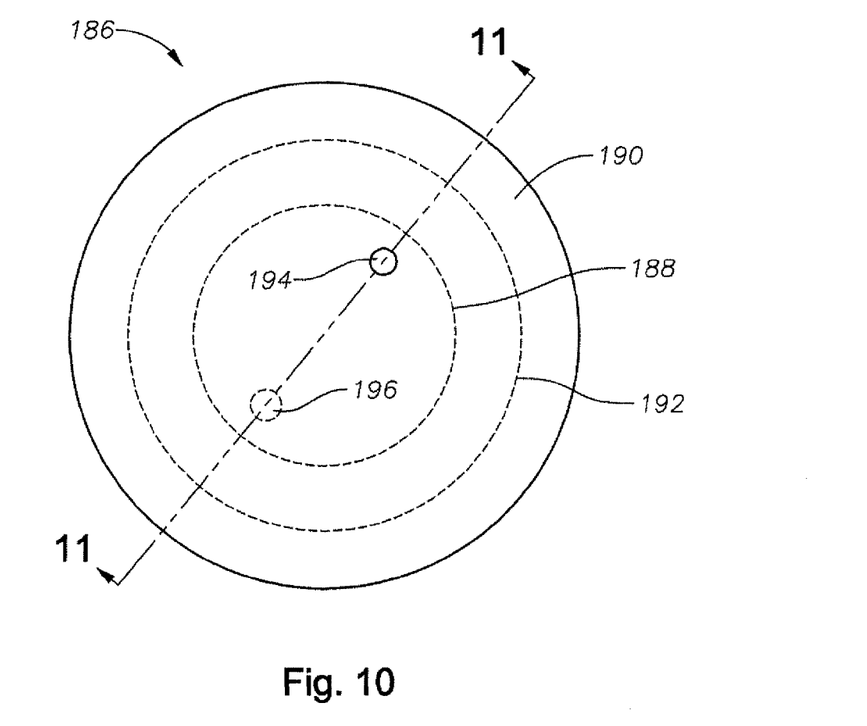
FIG. 10 is a top-view of another alternative embodiment of the transmissive patch of the negative pressure wound therapy apparatus of FIG. 1.
Figure 11:
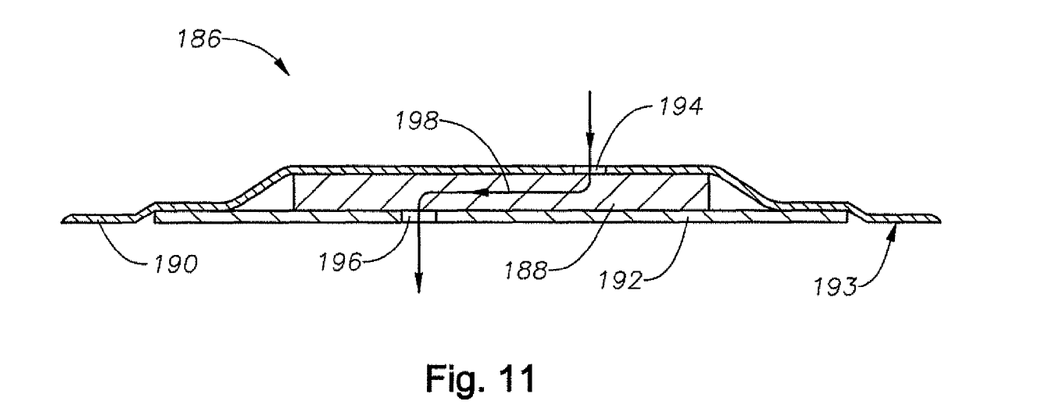
FIG. 11 is a sectional view of the embodiment of the transmissive patch of FIG. 10, taken along the 11-11 line.

Referring to FIGS. 10 and 11, in another embodiment, wherein vent patch 186 can include a semi-permeable barrier 188 that is sandwiched between cover layer 190 and bottom layer 192. In this embodiment, cover layer 190 can extend laterally beyond bottom layer 192, such that adhesive surface 193 can adhere to flexible sheet 116 (FIG. 1), as well as bottom layer 192 and semi-permeable barrier 188. The seal formed between cover layer 190 and flexible sheet 116 (FIG. 1) is generally airtight such that it prevents fluids such as air or liquids from passing between cover layer 190 and flexible sheet 116 (FIG. 1). Vent patch 186 can be any shape including, for example, round, rectangular, or elliptical.

Inlet aperture 194 can be a hole or other perforation through cover layer 190. Outlet aperture 196 can be a hole or other perforation through adhesive layer 192. In a preferred embodiment, outlet aperture 196 is located over dressing aperture 123 (FIG. 1). Inlet and outlet apertures 194, 196 can each be any size. They can be, for example, 1 mm in diameter, a pin-hole, or any other size or shape. In one embodiment, outlet aperture 196 is larger than inlet aperture 194 which can make it easier to align outlet aperture 196 with dressing aperture 123.

When suction is applied to dressing space 122 (FIG. 1), flow path 198 is created, wherein air or other fluid located outside of vent patch 186 passes through inlet aperture 194, through semi-permeable barrier 188, through outlet aperture 196, through dressing aperture 123 (FIG. 1), and into dressing space 122 (FIG. 1). The rate of fluid flow is controlled by the thickness of semi-permeable barrier 186, the lateral distance between inlet aperture 194 and outlet aperture 196, and the level of negative suction.

Referring back to FIGS. 1 and 2, a health-care provider applies packing 112, drain 114, and flexible sheet 116 over wound bed 100. In one embodiment, the health-care provider connects tube 106 to collection canister 108, which is connected to vacuum source 104. The health-care provider can activate vacuum source 104 to confirm that dressing 102 has proper seal integrity including, for example, having an adequate seal against skin 119. The health-care provider can then create dressing aperture 123 in flexible sheet 116, or locate dressing aperture 123 if dressing aperture 123 already exists in flexible sheet 116. Dressing aperture 123 may be a pin hole, a small incision, or any other type of opening. Preferably, the size of dressing aperture 123 is smaller than the size of semi-permeable barrier 124, such that semi-permeable barrier 124 is able to completely cover dressing aperture 123. Dressing aperture 123 can be located at any location on flexible sheet 116. Preferably, dressing aperture 123 is located over wound bed 100.

The caregiver then applies transmissive patch 118 over dressing aperture 123. Transmissive patch 118 may be preassembled, with semi-permeable barrier 124 already adhered to cover layer 126, or care giver may individually apply semi-permeable barrier 124 and cover layer 126 over dressing aperture 123. Cover layer 126 adheres to flexible sheet 116 and to semi-permeable barrier 124. In one embodiment, transmissive patch 118 can be attached to flexible sheet before it reaches the care giver. For example the manufacturer can attach transmissive patch 118 to flexible sheet 116 at the manufacturing facility, or a technician can attach transmissive patch 118 to flexible sheet 116 in a preparation area prior to distributing the pre-assembled unit to the care giver.

Cover layer 126 forms a seal around outer edge of semi-permeable barrier 124, thus preventing air or fluids from passing between the surface of flexible sheet 116 and the edge of semi-permeable barrier 124. Air is able to pass through openings 128 of cover layer 126 and then permeate through semi-permeable barrier 124 into dressing space 122. The transmission rate of semi-permeable barrier may work to reduce the volume and velocity of air passing through dressing aperture 123. Various sizes of dressing apertures 123, combined with various materials, thicknesses, and sizes of semi-permeable barrier 124 may be used to permit a desired flow rate through dressing aperture 123. The permeation of air through semi-permeable barrier 124 and dressing aperture 123 into the dressing space 122 can create the desired pressure differential to allow air and other fluids to move from dressing space 122 toward the vacuum source 104.

Semi-permeable barrier 124 can prevent fluids, bacteria, or germs originating within dressing space 122 from leaking out of dressing 102. Any fluids or germs that are able to move through dressing aperture 123 are blocked by semi-permeable barrier 124. Cover layer 126 prevents fluids and germs from passing between semi-permeable barrier 124 and flexible sheet 116. Furthermore, bacteria and germs originating outside of dressing 102 are not able to pass through semi-permeable barrier 124 into dressing space 122.

While the invention has been shown or described in only some of its forms, it should be apparent to those skilled in the art that it is not so limited, but is susceptible to various changes without departing from the scope of the invention.

Furthermore, recitation of the term about and approximately with respect to a range of values should be interpreted to include both the upper and lower end of the recited range. As used herein, the terms first, second, third and the like should be interpreted to uniquely identify elements and do not imply or restrict to any particular sequencing of elements or steps.

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

The singular forms "a", "an" and "the" include plural referents, unless the context clearly dictates otherwise.

Optional or optionally indicates that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

In the drawings and specification, there have been disclosed a typical preferred embodiment of the invention, and although specific terms are employed, the terms are used in a descriptive sense only and not for purposes of limitation. The invention has been described in considerable detail with specific reference to these various illustrated embodiments. It will be apparent, however, that various modifications and changes can be made within the spirit and scope of the invention as described in the foregoing specification and as defined in the appended claims.

I claim:

1. An apparatus for treating wounds, the apparatus comprising:
    a drain;
    a flexible sheet for covering a wound bed, the flexible sheet having a dressing aperture therethrough and being adapted to sealingly engage tissue proximate to the wound bed while the drain is located between the flexible sheet and the wound bed;
    a tube in communication with the drain; and
    a flow restriction device covering the dressing aperture, the flow restriction device comprising a semi-permeable barrier located between a first layer having a first aperture and a second layer having a second aperture, and wherein at least a portion of the second layer sealingly engages the flexible sheet and the second aperture is in communication with the first aperture, the flow restriction device reducing a flow of vapor and substantially preventing a flow of liquid through the dressing aperture.

2. The apparatus according to claim 1, wherein the flow restriction device has a higher rate of vapor transmission than the flexible sheet.

3. The apparatus according to claim 1, wherein the flexible sheet is semi-permeable to vapor and generally impermeable to liquid.

4. The apparatus according to claim 1, further comprising a vacuum source in communication with the tube.

5. The apparatus according to claim 4, wherein the vacuum source creates a negative pressure at the vacuum source, the negative pressure is communicated through the tube and the drain to the wound bed, and wherein the pressure in the wound bed is greater than the pressure at the vacuum source.

6. The apparatus according to claim 1, wherein the flow restriction device comprises high-density polyethylene fibers.

7. The apparatus according to claim 1, wherein the flow restriction device has a predetermined vapor transmission rate at a given pressure.

8. The apparatus according to claim 1, wherein the portion of the second layer of the flow restriction device comprises an adhesive.

9. A system for treating a wound, the system comprising:
    a flexible sheet, the flexible sheet being adapted to cover a wound bed and sealingly engage tissue adjacent to the wound bed;
    a dressing aperture through the flexible sheet;
    a flow restriction device covering the dressing aperture and sealingly engaging the flexible sheet, the flow restriction device comprising a semi-permeable barrier located between a first layer having a first aperture and a second layer having a second aperture, wherein at least a portion of the second layer sealingly engages the flexible sheet and the second aperture is in communication with the dressing aperture, the flow restriction device permitting vapor to pass therethrough while preventing liquid from passing therethrough;
    a drain located below the flexible sheet;
    packing located surrounding at least a portion of the drain;
    a tube in communication with the drain; and
    a vacuum source in communication with the drain.

10. The system according to claim 9, wherein the portion of the second layer of the flow restriction device comprises an adhesive.

11. The system according to claim 9, wherein a flow rate of vapor passing through the flow restriction device is greater than a flow rate of vapor passing through the flexible sheet.

* * * * *